| United States Patent [19] | [11] 3,996,155 |
|---|---|
| Slovinsky et al. | [45] Dec. 7, 1976 |

[54] PROCESS FOR MAKING BIS TRICHLOROMETHYL SULFONE EMULSIONS

[75] Inventors: Manuel Slovinsky, Woodridge; Kenneth G. Phillips, River Forest; Dodd Wing Fong, Woodridge, all of Ill.

[73] Assignee: Nalco Chemical Company, Chicago, Ill.

[22] Filed: Nov. 11, 1974

[21] Appl. No.: 522,950

[52] U.S. Cl. ............................... 252/312; 252/314; 260/607 A; 424/149; 424/170; 424/288; 424/302; 424/325; 424/337
[51] Int. Cl.² .......................................... B01J 13/00
[58] Field of Search ........... 252/312; 424/170, 337; 260/607 A

[56] References Cited

UNITED STATES PATENTS

| 1,440,356 | 12/1922 | Morrell | 252/311.5 |
| 1,993,706 | 3/1935 | Langwell | 252/312 |
| 3,138,519 | 6/1964 | Riden, Jr. et al. | 424/337 |
| 3,426,134 | 2/1969 | Shema et al. | 424/337 X |

*Primary Examiner*—Richard D. Lovering

[57] ABSTRACT

Oil-in-water type emulsions of bis trichloromethyl sulfone which can be made from dimethyl sulfide and sodium hypochlorite. Emulsification is achieved by using the by-product aqueous brine solution from the formation reaction thereby avoiding the ecological problem of brine waste disposal and resulting in a simple one-pot type emulsion preparation procedure. The technique is also particularly well adapted to making mixed biocide concentrate formulations containing emulsified bis trichloromethyl sulfone.

11 Claims, No Drawings

PROCESS FOR MAKING BIS TRICHLOROMETHYL SULFONE EMULSIONS

BACKGROUND OF THE INVENTION

The known biocide, bis trichloromethyl sulfone, has heretofore been prepared by various routes, one being the oxidation of dimethyl sulfoxide with sodium hypochlorite. The bis trichloromethyl sulfone product was then separated, and, typically, dried.

Since bis trichloromethyl sulfone is poorly soluble in water, it was heretofore apparently customary to dissolve this material in an organic solvent medium for which it was necessary to isolate bis trichloromethyl sulfone once after the synthesis reaction and dry it. Such prior art procedure suffers from serious disadvantages. For one thing, the aqueous brine solution inherently resulting as a by-product when sodium hypochlorite is used to oxidize dimethyl sulfoxide to bis trichloromethyl sulfone must be disposed of, which presents serious environmental pollution problems, particularly since the level of sodium chloride in the brine can approach saturation levels (e.g. about 30 weight percent). For another thing, the rewetting and suspending of bis trichloromethyl sulfone powder in water to make an emulsion, represents a time consuming, labor consuming operation. In addition, when it is desired to blend with a bis trichloromethyl sulfone solution in organic solvent one or more additional biocides to broaden the spectrum of biocidal activity for the resulting composition, an entire series of special formulation preparation procedures were heretofore conventional and apparently considered essential to the making of a desired liquid composition containing dissolved bis trichloromethyl sulfone. See for example, U.S. Pat. No. 3,426,134 to Shema, Reilly, and Kubasko.

There are growing objections to the use of organic solvents in formulating biocides. For one thing, solvents cause ecological problems. Thus, organic solvents can cause acceleration in the ability of a biocide to penetrate human skin so that in the case of spills or accidental contact, the danger to human life is increased by the presence of such solvents. Water based systems do not penetrate skin as rapidly, and therefore, water based systems are somewhat safer to use. For another thing, solvents raise economic problems, owing to recent raises in the prices of organic solvents commonly used in formulating biocides. For still another thing, solvents can offer processing problems, so that the effect is to increase the cost of biocidal formulations containing organic solvents. Thus, for example, previously bis trichloromethyl sulfone was produced and separated (dried) before ever being formulated in non-aqueous solvent systems; brine generated in production thus presented disposal problems, as indicated above. Control of solvent vapors during formulation preparation can be a problem.

It has now been discovered that bis trichloro methyl sulfone is unexpectedly well adapted for emulsification to form emulsions of the oil-in-water type. It happens that this material melts at a relatively low temperature (about 35° C) and can be warmed to higher temperatures without decomposition. Thus, when the liquid material is heated to about 60° to 70° C, and agitated with a surfactant (or emulsifier) in the presence of deionized water, it has now been discovered that a true liquid/liquid emulsion of the oil in water type results which contains absolutely no organic solvent.

It has been now further discovered that bis trichloromethyl sulfone surprisingly can be emulsified in the brine water produced during its synthesis by the route above indicated. It is generally difficult to emulsify materials in brine. The high ionic content in brine works against emulsification therein because such tends to upset the delicate interaction of electric charges permitting formation of the dispersed phase in the continuous phase. Indeed, an increase in ion content is a conventional means used to coagulate an emulsion. It is unexpected that coagulation does not occur in such brine water os bis trichloromethyl sulfone emulsified therein, and the result could not have been predicted.

Emulsification of bis trichloromethyl sulfone in its own (waste) brine water not only saves the trouble and expense of further separating and drying the material, as heretofore done in this art, but also solves a difficult ecological problem of disposing of the brine water. Such emulsification avoids the need to isolate the product out of the reaction and then going back into a reactor for formulation. Such emulsification avoids altogether the use of organic solvents. Further, other biocides can be readily compounds with the bis trichloromethyl sulfone in a product emulsion without adversely affecting emulsion desired characterstics, thereby broadening the spectrum of biocidal activity for a resulting mixed system. A product emulsion can generally be infinitely diluted which permits such to be employed in the end use applications directly without intermediate treatment or dilution where the bis trichloromethyl sulfone is used at a rate of the order of parts per million in a water system (e.g. in cooling towers and the like). Surprisingly, a product emulsion of this invention containing brine water has improved freeze/thaw stability over such an emulsion containing no dissolved salts.

Thus, there has now been discovered a new technique for preparing bis trichloromethyl sulfone aqueous emulsions of the oil in water type which avoids the disadvantages associated with the prior art technology and enables one to prepare new and very useful emulsions of bis trichloromethyl sulfone. These new emulsions can be prepared so as to contain bis trichloromethyl sulfone over a variety of concentrations, and the technique involved readily permits the introduction of other biocides into the product emulsion during preparation thereof in a simple but convenient and step-saving manner.

BRIEF SUMMARY OF THE INVENTION

In one aspect, this invention relates to a process for making bis trichloromethyl sulfone involving the adding of dimethyl sulfide to an aqueous liquid system containing not more than about 22 weight percent total system basis alkali metal hypochlorite. The addition rate of the dimethyl sulfide is such that the temperature of the liquid phase system is maintained in the range from about 30 to 60° C. Thereafter, one maintains the resulting liquid phase system at a temperature in the range from about 40° to 105° C for a time sufficient to produce the desired bis trichloromethyl sulfone.

In another aspect, the present invention involves a process for making an oil-in-water type emulsion of bis trichloromethyl sulfone in which the product of the above described reaction of dimethyl sulfide with hypochlorite, including the aqueous by-product brine solution, is admixed with a surfactant having an HLB balance number in the range of from 2 to 40, and agitated to emulsify the resulting mixture, thereby to produce an emulsion in which the dispersed phase comprises bis trichloromethyl sulfone and the continuous phase being comprised of brine water, at least partially In another aspect, this invention is directed to an aqueous liquid emulsion which comprises, on a 100 weight percent total emulsion basis, from about 1 to 50 weight percent of a disperse phase comprised of bis trichloromethyl sulfone and from about 50 to 99 weight percent of a continuous phase. The continuous phase is comprised, on a 100 weight percent total continuous phase basis, of from about 0.1 to 70 weight percent dissolved additives, and, correspondingly, from about 30 to 99.9 weight percent water.

The dissolved additives in the continuous phase comprise on a 100 weight percent total emulsion basis, from 0 to about 15 weight percent alkali metal hydroxide, from 0 to about 30 weight percent of at least one material selected from the class consisting of alkali metal chloride and alkali metal salts more soluble in water than alkali metal chloride, and from 0 to about 10 weight percent of alkali metal hypochlorite. In addition, the emulsion has dissolved therein from about 0.5 to 25 weight percent on a 100 weight percent total emulsion basis of surfactant having an HLB balance number as indicated. The dispersed phase of the emulsion is in the physical form of discrete globules whose average individual diameters fall in the range of from about 2 to 2000 microns.

The present invention provides improved aqueous emulsions of bis trichloromethyl sulfone which avoid prior art preparation problems including that of brine disposal. The product emulsions are adapted to have improved biocidal activity for the various applications in which bis trichloromethyl sulfone has theretofore been employed. For example, as an additive at the rate of about 10 parts per million to water circulated in cooling towers and the like.

DETAILED DESCRIPTION

In making bis trichloromethyl sulfone, by the teachings of this invention, it is preferred that the total amount of dimethyl sulfide added to aqueous alkali metal hypochlorite range from about 80 percent up to 100 percent of the total stoichiometric amount of alkali metal hypochlorite present. Sodium hypochlorite is the preferred alkali metal hypochlorite. More preferably, the total amount of dimethyl sulfide so added is approximately equal to the stoichiometric amount of alkali metal hypochlorite present. When less than a stoichiometric amount of dimethyl sulfide is so added, an excess of alkali metal hypochlorite remains in a reaction product at the close of dimethyl sulfide addition. Since, as those skilled in the art appreciate, alkali metal hypochlorite itself is a biocide, it is possible by this means to prepare a composition containing two different biocides, the bis trichloromethyl sulfone being a non-oxidizing biocide, while the alkali metal hypochlorite is an oxidizing biocide.

When it is desired to produce a reaction product containing substantially no unreacted alkali metal hypochlorite, and/or when it is desired to produce a reaction product in which a maximum conversion of starting materials to bis trichloromethyl sulfone, after the adding of dimethyl sulfide has been completed, the resulting aqueous phase system is preferably subjected to reflux conditions for a time interval preferably in the range of from about 30 minutes to 2 hours, and more preferably in the time interval ranging from about 45 minutes to one and a half hours, though longer and shorter times may be employed. For this process step, a conventional reflux condenser arrangement can be associated with a reactor vessel, as those skilled in the art will readily appreciate.

In one mode, the addition of dimethyl sulfide to aqueous alkali metal hypochlorite may be accomplished under slightly elevated pressures above atmospheric so as to minimize losses of dimethyl sulfide, although dimethyl sulfide rapidly reacts with aqueous alkali metal hypochlorite so that loss of dimethyl sulfide through vaporization is characteristically minimal, nevertheless for efficient process operation, it is preferred to minimize any loss of dimethyl sulfide through vaporization. For this purpose, the temperature of the aqueous liquid phase system during dimethyl sulfide addition may be maintained below the boiling point of the dimethyl sulfide, e.g., about 36° to 37.5° C, the atmospheric boiling point of dimethyl sulfide, at atmospheric pressure. Alternatively, the reaction vessel may be equipped with a reflux condenser adjusted to condense dimethyl sulfide vapors escaping from the reaction zone, which vapors may then either be stored or returned directly to the reaction zone as desired.

In one preferred mode of operating, the aqueous liquid phase system to which the dimethyl sulfide is added contains from about 12 to 20 weight percent alkali metal (preferably sodium) hypochlorite. Conveniently and preferably, the alkali metal hypochlorite may be generated in situ by the conventional procedure of chlorine addition to aqueous alkali metal hydroxide solution, as those skilled in the art will appreciate.

When dimethyl sulfide is added to the aqueous liquid phase containing sodium hypochlorite, this liquid phase should preferably be below the boiling point of dimethyl sulfide, so there is no need for reflux or the like to collect vaporized dimethyl sulfide or the like. If this liquid phase is above the boiling temperature of dimethyl sulfide, reaction still occurs, as desired, but a high concentration of vaporized dimethyl sulfide is preferably avoided.

The process of this invention may be practiced batchwise or continuously.

As indicated, the rate of addition of dimethyl sulfide to the aqueous alkali metal hypochlorite is controlled so that the temperature of the liquid phase reaction system does not rise above about 60° C. Although somewhat higher temperatures can be employed, at such elevated temperatures, there may be a tendency for the alkali metal hypochlorite to display some degradation, and, also at such higher temperatures, some increase in the undesirable vaporization of dimethyl sulfide can occur between addition thereof and reaction thereof.

Addition of dimethyl sulfide to aqueous alkali metal hypochlorite induces a vigorous, exothermic reaction. In addition to regulating the rate of addition of dimethyl sulfide, reaction temperatures are preferably controlled by means of a cooling jacket about the reactor. The dimethyl sulfide may be added continuously or incrementally as desired.

The product existing at the close of dimethyl sulfide addition, or, if a step of refluxing is employed, at the close of reflux, is a two-phase heterogeneous system. If agitation (stirring is stopped at this point, the phases separate into a lower phase and an upper phase. The lower phase comprises bis trichloromethyl sulfone and is essentially a non-aqueous layer except possibly for some entrapped water therein. The upper phase is an aqueous solution of alkali metal chloride, alkali metal hydroxide, and, if present, alkali metal hypochlorite. During reflux and during addition of dimethyl sulfide to aqueous alkali metal hypochloride, the reaction liquid mixture is preferably continuously agitated. There is no need to cease agitation at the termination of dimethyl sulfide addition, or at the termination of reflux, as the case may be, before proceeding to the next or emulsification step sequence.

After the heating step at 40° to 105° C, it is preferred but not necessary, to neutralize or partly neutralize the resulting mixture through addition thereto of a material selected from the group consisting of hypochloric acid and acidic material which forms alkali metal salts in water solution which are generally more soluble in water than alkali metal chloride. After the heating step, the pH of the system is typically above about 12. After the addition of acidic material the pH of the system typically is in the range from about 0.1 to 12. The reaction generates NaOH. Examples of suitable acids for neutralizing or partially neutralizing, the system through addition thereto of hydrochloric acid and/or an acidic material which forms alkali metal salts (preferably sodium) which are more soluble in water than such alkali metal chloride include formic acid, acetic acid, phosphoric acid, and the like. Such a neutralization can be advantageous since the amount of alkali metal chloride present in a product reaction mixture can be near the saturation point, so that during subsequent cooling of the system, undesirable precipitation of alkali metal chloride crystals can occur at high alkali metal chloride concentrations. In general, for reasons of process efficiency, it is preferred to so select reactants that there is produced in the product liquid phase a level of alkali metal chloride in the range from about 20 weight percent up to solution saturation as respects the total weight of the aqueous liquid phase.

In emulsification, one admixes with the resulting system, with agitation, at least one surfactant. Surfactants used preferably have an HLB balance number in the range of from about 2 to 40. Examples of suitable surfactants include adducts of an alkyl phenol and ethylene oxide, adducts of sorbitol mono oleate with ethylene oxide, ethylene oxide/propylene oxide block copolymers, and the like. The weight ratio of surfactant to bis trichloromethyl sulfone ranges from about 1:20 to 1:1.

One sufficiently agitates the resulting mixture to emulsify the bis trichloromethyl sulfone and form a dispersed phase thereof in a continuous aqueous phase. Preferably, surfactant addition and agitation sufficient to emulsify are conducted simultaneously, but they may be conducted sequentially with surfactant addition preceding emulsification agitation. Emulsification is preferably conducted at a temperature sufficient to maintain the bis trichloromethyl sulfone in a liquid condition. For example, atmospheric pressures and a temperature in the range from about 36° to 120° C is preferably employed, with a maximum temperature of more preferably below about 100° C.

A product emulsion is preferably cooled with agitation to room temperature after formation thereof. Characteristically a product emulsion is stable at room temperature, and the disperse phase is in the physical form of discrete globules with average individual diameters in the range of from about 2 to 2000 microns.

Typically, emulsions of this invention are water dilutable and, as prepared, typically have viscosities in the range of from about 2 to 2000 centipoises.

After preparation, a product emulsion may be passed through a homogenizer which functions, apparently, to further stabilize the emulsion, to decrease the average globule size, and to increase the viscosity thereof. Any conventional homogenizer apparatus may be employed, depending upon the scale of preparation, such as a laboratory hand-operated Fisher homogenizer, or a semi-works size Manton-Gaulin homogenizer.

It is preferred to add an emulsion of this invention preferably during the emulsification thereof, a water-soluble viscosity thickener in an amount ranging from about 0.05 to 10 weight percent on a 100 weight percent total emulsion basis. Typically, such viscosity thickener is soluble in the aqueous phase. Such viscosity thickeners are well known to the art and aid in stabilizing an emulsion presumably by slowing any tendency for sedimentation or the like. One presently preferred suitable viscosity thickener is an extra-cellular polysaccharide.

By using the by-product/aqueous brine solution for emulsification, one can characteristically produce a product emulsion containing a total of about 7 weight percent bis trichloromethyl sulfone at the maximum, though, of course, lesser amounts of bis trichloromethyl sulfone may be present, depending upon the concentration of these reactants used.

In order to increase the concentration in a product emulsion of bis trichloromethyl sulfone, either one or both of two things may be done: (1) After dimethyl sulfide addition (or after reflux if such is employed) and before surfactant addition, with agitation, one may remove from 0 up to about 95 weight percent of the total amount of the aqueous brine phase present in a reaction product (the reaction product being first allowed to separate into its respective phases). (2) After dimethyl sulfide addition (or after reflux if such is employed) and before surfactant addition, with agitation, one may add with mixing from 0 up to about 45 weight percent of separately prepared bis trichloromethyl sulfone, total resulting system weight basis, while maintaining a temperature in the range of from about 38° to 100° C.

By practicing such techniques, a wide range of variation in the bis trichloromethyl sulfone content of a product liquid emulsion is achievable. Thus, a product aqueous liquid emulsion comprises on a 100 weight percent total emulsion basis, from about 1 to 50 weight percent of a disperse phase comprised of bis trichloromethyl sulfone, and from about 50 to 99 weight percent of a continuous phase. The continuous phase contains dissolved additives in the respective weight percentages above indicated, in general. Preferably, the continuous phase is comprised on a 100 weight percent total continuous phase basis of from about 0.1 to 70 weight percent dissolved additives, and correspondingly, from about 30 to 99.9 weight percent water. Similarly, the dissolved additives preferably comprise on a 100 weight percent total emulsion basis, from 0 to about 15 weight percent alkali metal (preferably sodium) hydroxide, from 0 to about 30 weight percent of at least one material selected from the class consisting of alkali metal chloride (preferably sodium) and alkali metal (preferably sodium) salts more soluble in water than such alkali metal chlorides, and from 0 to about 10 weight percent of alkali metal hypochlorite (preferably sodium).

For ecological reasons related to disposing of by-product brine, it is presently preferred to produce emulsions of this invention which contain at least about 10 weight percent dissolved alkali metal chloride in the continuous phase (total emulsion weight basis).

Preferred surfactants have an HLB balance number in the range from about 6 to 14, and preferably the emulsion has dissolved therein from about 0.05 to 25 weight percent, on a 100 weight percent total emulsion basis, of surfactant. Nonionic surfactants are presently preferred.

The present invention readily permits one to prepare aqueous systems containing therein mixed biocides, one of the biocides being the bis trichloromethyl sulfone, emulsified as above described. The mixture of bis trichloromethyl sulfone with dissolved alkali metal hypochlorite, the amount of hypochlorite present ranging up to about 5 weight percent total emulsion weight basis, is prepared as described above conveniently by permitting amounts of dimethyl sulfide lower than stoichiometrically required to react with and alkali metal hypochlorite. Sodium hypochlorite, for example, may be added to a product emulsion if desired. Biocides which are poorly soluble in water other than bis trichloromethyl sulfone may be introduced into a reaction product before addition of surfactant thereto, conveniently, particularly when such added biocide is emulsifiable under the same temperature and surfactant addition and agitation conditions that the bis trichloromethyl sulfone is emulsified under as described above. Examples of suitable such additional added biocides include methylene bis thiocyanate, bis(tri-n-butyl tin) oxide, biocidal amines, biocidal quaternary ammonium compounds, and the like. Typically and preferably, such a mixture of bis trichloromethyl sulfone and at least one other biocide, has a weight ratio of bis trichloromethyl sulfone to such other biocide, ranging from about 1:25 to 25:1. Solubility of non-solubility in water of such other biocide is not a limiting factor, but in the case where such other biocide is not soluble in water, it should be emulsifiable in water. Typically, emulsions of this invention are water dilutable without deterioration, as is needed in those conventional applications where the biocide is used at extremely dilute levels, for example, in terms of from about 1 to 100 parts per million of total biocide in water used in, for example, cooling towers and the like.

So far as is known, no one has heretofore ever prepared aqueous emulsions of bis trichloromethyl sulfone using the by-product aqueous beine as the water for emulsification, and, furthermore, it is believed that no one has heretofore prepared biocide mixtures with bis trichloromethyl sulfone in emulsion form using such brine liquid, thereby overcoming the previous difficulties of manufacture, and also providing new and superior biocide emulsion formulations in concentrate form. Sometimes one may use alkaline earth metal hypochlorites in place of alkali metal hypochlorites.

EMBODIMENTS

The present invention is further illustrated by reference to the following Examples. Those skilled in the art will appreciate that other and further embodiments are obvious and within the spirit and scope of this invention from the teachings of these present Examples taken with the accompanying Specification.

EXAMPLE 1

Sodium hypochlorite solution is first prepared by charging 57 grams of chlorine gradually into 260 grams of 25% NaOH aqueous solution at a temperature not above 30° C (addition of chlorine into the NaOH being an exothermic reaction). About 0.02 mole of NaOH is present in the product solution.

Then 6.2 grams of dimethyl sulfide (0.1 mole) is added into the resulting sodium hypochlorite solution gradually with agitation. The reaction is exothermic. The temperature of the reaction mixture is not allowed to rise above about 60° C. The reaction vessel is jacketed. Atmospheric conditions are used.

Next, the resulting mixture is heated and refluxed with agitation for about 45 minutes. The mixture is then cooled to about 70° C and is found to have a pH about 12. Substantially all of the sodium hypochlorite is consumed and a yield of about 75 weight percent bis trichloromethyl sulfone is produced (based on dimethyl sulfide).

At this point with agitation being continuously maintained, 22 to 23 grams of formic acid is now added to reduce the pH to about 5. Sodium formate is more soluble than sodium chloride.

With vigorous stirring, 3.6 grams "Tween 81", a trademark of the Atlas Chemical Industries, Inc. for one of its brands of polyoxyethylene derivatives of fatty acid partial esters of sorbitol anhydride (an ethylene oxide adduct of sorbitan mono oleate) are added to the product aqueous system maintained at about 70° C which is about 1 percent of the total system. While in this instance the stirred heterogeneous system is not allowed to separate before addition of the "Tween 81", separation into two phases before adding "Tween 81" does not adversely affect emulsification. The product is an emulsion of oil-in-water type wherein the globules of the disperse phase fall in the size range of from about 2 to 2000 microns. The disperse phase which is comprised of bis trichloromethyl sulfone comprises about 6.2 weight percent with, correspondingly, the weight percent of the continuous phase being about 93.8 weight percent on a total emulsion weight basis. The continuous phase is comprised of about 28.5 weight percent dissolved additives with the balance up to 100 weight percent thereof being water on a total continuous phase weight basis. Dissolved in the aqueous phase are about 8.7 weight percent sodium formate and about 19.7 weight percent sodium chloride on a 100 weight percent total emulsion basis.

EXAMPLE 2

About 1.75 grams of "Kelzan", a trademark of the Kelco Company for its brand of extra-cellular polysaccharide are admixed with the emulsion of Example 1 so as to introduce into the product emulsion about 0.5 weight percent of this thickener. The "Kelzan" is first wetted with ethanol to form a paste in order to facilitate solution of this material in the emulsion. The viscosity of this product emulsions is observed to be greater than the viscosity of the starting emulsion of Example 1.

This dissolution is accomplished at a temperature of about 60° to 70° C in about 20 minutes after which the product emulsion is cooled to room temperature with stirring. This product has a milky appearance and is stable on standing. The product emulsion is water dilutable without emulsion phase separation. When water diluted down to 500 parts per million, it displays excellent biocidal activity.

EXAMPLE 3

Sodium hypochloride solution is prepared as taught in Example 1.

About 0.08 mole of dimethyl sulfide is gradually added into the resulting sodium hypochlorite solution at a rate sufficient to permit maintaining the liquid phase temperature below about 60° C. The reaction vessel is jacketed.

Thereafter, the resulting liquid phase mixture is maintained at about 75° C for about 3 hours. After cooling to about 70° C, the system is found to have a pH above 12. Sufficient concentrated hydrochloric acid is admixed with the system to reduce the pH to about 10.

About 2 weight percent on a 100 weight percent total emulsion basis of "Surfonic N-95", a trademark of Jefferson Chemical Co., for its brand of alkylaryl polyethylene glycol ether non-ionic surfactants, are added with vigorous stirring to the product system which is maintained at about 70° C. The product is an emulsion of oil-in-water type wherein the globules of the disperse phase are estimated to fall in the size range of from about 2 to 2000 microns. The disperse phase, which is comprised of bis trichloromethyl sulfone, comprises about 2.5 to 3 weight percent thereof, with the continuous phase comprising about 97 to 97.5 weight percent of the emulsion on a total 100 weight percent emulsion basis. The continuous phase is comprised of about 24 weight percent dissolved additives with the balance up to 100 weight percent thereof being water on a total continuous phase weight basis. Dissolved in the aqueous phase are about 20 weight percent sodium chloride, about 7 weight percent sodium hydroxide, and about 0.2 weight percent sodium hypochlorite on a total emulsion weight basis.

EXAMPLE 4

The procedure of Example 1 is repeated except that Tergitol 12-P-6 surfactant is employed in place of the "Tween 81". Tergitol 12-P-6 is a trademark of Union Carbide Co. for its brand of alkyl phenol adduct with ethylene oxide. A similar product emulsion obtained is that of Example 1.

EXAMPLE 5

The procedure of Example 2 is repeated using the emulsion product of Example 4. A similar product emulsion is obtained to that of Example 2.

EXAMPLE 6

To an emulsion prepared in the manner of Example 2 but having a pH between 8 and 9 is added with mixing about 1 weight percent of bis(tri-n-butyl tin) oxide (based on total emulsion weight). This added material is initially in liquid form. The product emulsion is stable and water dilutable and displays excellent biocidal activity.

EXAMPLE 7

To an emulsion prepared in the manner of Example 2 but having a pH below 7 is added with mixing 5 weight percent (based on total emulsion weight) of cyano ethyl coco diamine; this added material is initially in liquid form. The pH of the product emulsion is adjusted to a pH of 4.5 with hydrochloric acid. The product emulsion is stable, and water dilutable, and displays excellent biocidal activity.

EXAMPLE 8

To an emulsion at 95° C. prepared in the manner of Example 2 but having a pH below 7 is added with mixing 5 weight percent (based on total emulsion weight) of methylene bis thiocyanate; this added material is initially in powder form at room temperature. The pH of the product emulsion is adjusted to a pH of 4.5 with hydrochloric acid. The product emulsion is stable, and water dilutable, and displays excellent biocidal activity.

We claim:

1. A process for making an aqueous liquid emulsion of bis trichloromethyl sulfone comprising the steps of:
   a. adding dimethyl sulfide in a liquid phase to an aqueous liquid phase system containing initially not more than about 22 weight percent total system basis of alkali metal hypochlorite, the addition rate of said dimethyl sulfide being such that the temperature of the resulting liquid phase system is maintained in the range from about 30° to 60° C.
   b. maintaining after said adding the resulting liquid phase system at a temperature in the range from about 40° to 105° C for a period of time sufficient to produce bis trichloromethyl sulfone,
   c. admixing with the resulting system surfactant having an HLB balance number in the range from about 2 to 40, the weight ratio of surfactant to bis trichloromethyl sulfone ranging from about 1:20 to 1:1, and
   d. agitating at a temperature ranging from about 36° to 120° C the resulting mixture sufficiently to emuslify the bis trichloromethyl sulfone so as to form a dispersed phase thereof in a continuous phase comprised of water.

2. The process of claim 1 wherein the total amount of dimethyl sulfide so added ranges from about 80 up to 100 weight percent of the total stoichiometric amount of alkali metal hypochlorite present.

3. The process of claim 1 wherein the total amount of dimethyl sulfide so added is approximately equal to the stoichiometric amount of alkali metal hypochlorite present.

4. The process of claim 1 wherein said liquid phase reaction system is maintained in an enclosed zone protected with a zone of reflux condensation whose condensed surfaces are adapted to condense vaporized dimethyl sulfide escaping from said liquid phase system.

5. The process of claim 1 wherein the temperature of said liquid phase system is maintained below the boiling point of dimethyl sulfide.

6. The process of claim 1 wherein the temperature of said aqueous liquid phase system is maintained below about 37.5° C.

7. The process of claim 1 wherein said liquid phase system contains from about 12 to 20 weight percent sodium hypochlorite.

8. The process of claim 1 wherein after said adding, the resulting aqueous liquid phase system is subjected to reflux conditions having a time interval range from about 30 minutes to 2 hours.

9. The process of claim 1 wherein after said step (b) and before said step (c), from 0 up to about 95 weight percent of the total amount of the aqueous phase present is separated from said resulting system.

10. The process of claim 1 wherein after said step (b) and before said step (c) from 0 up to about 45 weight percent, total resulting system weight basis, of bis trichloromethyl sulfone is admixed therewith while maintaining a temperature in the range from about 36° to 106° C.

11. The process of claim 1 wherein after said step (b) and before said step (c) said resulting liquid phase system is neutralized through addition thereto of at least one material selected from the group consisting of hydrochloric acid and an acidic material which forms alkali metal salts in water solution which are generally more soluble in water than said alkali metal chloride.

* * * * *